United States Patent [19]

Wang et al.

[11] Patent Number: 5,916,969
[45] Date of Patent: *Jun. 29, 1999

[54] ARTICLE AND COMPOSITION OF MATTER MADE FROM POLYOLEFINS AND PEO BLEND AND METHOD OF MAKING THE SAME

[75] Inventors: James Hongxue Wang; David Michael Schertz, both of Appleton, Wis.

[73] Assignee: Kimberly-Clark Corporation, Neenah, Wis.

[ * ] Notice: This patent is subject to a terminal disclaimer.

[21] Appl. No.: 08/755,516

[22] Filed: Nov. 22, 1996

[51] Int. Cl.⁶ .......................... C08L 71/02; C08L 51/06; C08L 23/00
[52] U.S. Cl. ......................... 525/64; 525/187; 525/303; 524/378
[58] Field of Search ................. 525/64, 187, 303; 524/378

[56] References Cited

U.S. PATENT DOCUMENTS

| | | | |
|---|---|---|---|
| 3,323,978 | 6/1967 | Rasmussen | 161/169 |
| 3,539,666 | 11/1970 | Schirmer | 264/51 |
| 3,717,541 | 2/1973 | Schirmer | 161/169 |
| 3,833,708 | 9/1974 | Miller et al. | 264/344 |
| 3,935,141 | 1/1976 | Potts et al. | 260/23 H |
| 3,954,928 | 5/1976 | Omori et al. | 264/51 |
| 4,018,729 | 4/1977 | Faucher et al. | 260/17 R |
| 4,080,405 | 3/1978 | Agouri et al. | 260/878 R |
| 4,186,233 | 1/1980 | Krajewski et al. | 428/213 |
| 4,229,334 | 10/1980 | Klabacka . | |
| 4,868,222 | 9/1989 | Chau et al. | 521/61 |
| 5,095,619 | 3/1992 | Davis et al. | 30/41 |
| 5,300,574 | 4/1994 | Bacskai | 525/181 |
| 5,367,003 | 11/1994 | Petcavich | 523/124 |
| 5,369,168 | 11/1994 | Famili et al. | 525/57 |
| 5,391,423 | 2/1995 | Wnuk et al. | 428/217 |
| 5,395,308 | 3/1995 | Fox et al. | 604/15 |
| 5,415,905 | 5/1995 | Middlesworth et al. | 528/35.7 |
| 5,417,679 | 5/1995 | Toms et al. | 604/370 |
| 5,429,874 | 7/1995 | VanPutte | 428/522 |
| 5,446,100 | 8/1995 | Durrance et al. | 525/221 |
| 5,468,259 | 11/1995 | Sheth et al. | 8/497 |
| 5,489,470 | 2/1996 | Noda | 428/286 |
| 5,498,692 | 3/1996 | Noda | 528/361 |
| 5,498,785 | 3/1996 | Wang et al. | 525/371 |
| 5,509,913 | 4/1996 | Yeo | 604/364 |
| 5,532,066 | 7/1996 | Latiolais et al. | 428/483 |
| 5,540,663 | 7/1996 | Kroner et al. | 428/221 |
| 5,549,791 | 8/1996 | Herron et al. | 162/157.6 |
| 5,589,545 | 12/1996 | Ramachandran | 525/187 |
| 5,700,872 | 12/1997 | Wang | 525/187 |

FOREIGN PATENT DOCUMENTS

| | | |
|---|---|---|
| A-52355/93 | 3/1994 | Australia . |
| 0 184 440 A2 | 6/1986 | European Pat. Off. . |
| 0 210 754 A1 | 2/1987 | European Pat. Off. . |
| 0 612 773 A1 | 8/1994 | European Pat. Off. . |
| 0 705 934 A3 | 4/1996 | European Pat. Off. . |
| 49-126742 | 12/1974 | Japan . |
| 181859 | 8/1986 | Japan . |
| 61-272217 | 12/1986 | Japan . |
| 1-246411 | 10/1989 | Japan . |
| 2 295 553 | 6/1996 | United Kingdom . |
| WO 94/00163 | 1/1994 | WIPO . |
| WO 94/00293 | 1/1994 | WIPO . |
| WO 95/11929 | 5/1995 | WIPO . |
| WO 95/20614 | 8/1995 | WIPO . |
| WO 95/20615 | 8/1995 | WIPO . |
| WO 95/20621 | 8/1995 | WIPO . |
| WO 95/23249 | 8/1995 | WIPO . |
| WO 95/23250 | 8/1995 | WIPO | D01D 5/40 |
| WO 96/20738 A1 | 7/1996 | WIPO . |
| WO 96/20831 A1 | 7/1996 | WIPO . |
| WO 96/21057 | 7/1996 | WIPO | D04H 1/42 |
| WO 96/21475 | 7/1996 | WIPO | A61L 15/30 |

OTHER PUBLICATIONS

Patent Cooperation Treaty Search Report from the International Search Authority, International Application No. PCT/US 97/19837 dated Feb. 4, 1988.

Patent Abstracts of Japan JP 61–181,859: Description of Shimizu Hideto, "Electrically Conductive Polymer Composition Having Positive Temperature Coefficient Characteristic."

Derwent World Patent Database abstract of JP 8–212,995: Description of Mitsubishi Paper Mills Ltd., "Non–Woven Cloth For Alkaline Battery Separator For High Electrolyte Absorptivity."

Bartczak, Z. and A. Galeski, "Changes in Interface Shape During Crystallization in Two–Component Polymer Systems," *Polymer*, 1986, vol. 27, Apr., pp. 544–548.

Mortensen, Kell, "Phase Behavior of Poly(propylene Oxide–)–Poly(ethylene oxide)–Poly(propylene oxide) Triblock Copolymer Melt and Aqueous Solutions," *Macromolecules*, vol. 27, No. 20, 1994, pp. 5654–5666.

Song, Z. and W. E. Baker, "Melt Grafting of T–Butylaminoethyl Methacrylate Onto Polyethylene," *Polymer*, 1992, vol. 33, No. 15, pp. 3266–3273.

Tang, Tao and Baotong Huang, "Compatibilization of Polypropylene/Poly (Ethylene Oxide) Blends and Crystallization Behavior of the Blends," *Journal of Polymer Science: Part B: Polymer Physics*, vol. 32, (1994), pp. 1991–1998.

Primary Examiner—David Buttner
Attorney, Agent, or Firm—Jones & Askew, LLP

[57] ABSTRACT

A water-responsive, thermoplastic article is formed from a composition of matter comprising a blend of polyolefins and poly(ethylene oxide). A water-dispersible article can be made from a blend having from about 1 weight percent to about 35 weight percent polyolefin and from about 99 weight percent to about 65 weight percent of poly(ethylene oxide). The water responsiveness of the article can be varied by modifying the polyolefin and increasing the content of polyolefin in the blend upwards to about 55 weight percent. The compositional blends can be made into a flushable barrier film for use in a disposable absorbent article, such as a diaper or feminine pad, or can be used to make a water responsive tampon tube. A method of making the article comprises blending together the polyolefin and poly(ethylene oxide) under melt conditions and forming the article.

26 Claims, 2 Drawing Sheets

5,916,969

ARTICLE AND COMPOSITION OF MATTER MADE FROM POLYOLEFINS AND PEO BLEND AND METHOD OF MAKING THE SAME

FIELD OF THE INVENTION

The present invention relates to a water-responsive article made from composition comprising a thermoplastic blend of hydrophilic and hydrophobic polymers. More particularly, the present invention relates to a water-responsive article made from a composition comprising a blend of polyolefin and poly(ethylene oxide) and a method of making the article from the blend.

BACKGROUND OF THE INVENTION

Personal care products, such as diapers, sanitary napkins, adult incontinence garments, and the like are generally constructed from a number of different components and materials. Such articles usually have some portion, usually the backing layer constructed of a liquid repellent film material. The liquid repellent film commonly used includes plastic materials such as a polyethylene film or copolymers of ethylene and other polar and nonpolar monomers. The purpose of the liquid repellent layer is to minimize or prevent absorbed liquid that may, during use, exude from the absorbent and soil the user or adjacent clothing. The liquid repellent film also has the advantage of allowing greater utilization of the absorbent capacity of the product.

Although such products are relatively inexpensive, sanitary and easy to use, disposal of a soiled product is not without its problems. Typically, the soiled products are disposed in a solid waste receptacle. This adds to solid waste disposal costs and presents health risks to persons who may come in contact with the soiled product. An ideal disposal alternative would be to use municipal sewage treatment and private residential septic systems by flushing the soiled product in a toilet. Products suited for disposal in sewage systems are termed "flushable." While flushing such articles would be convenient, the liquid repellent material normally does not disintegrate in water. This tends to plug toilets and sewer pipes, frequently necessitating a visit from the plumber. At the municipal sewage treatment plant the liquid repellent material may disrupt operations by plugging screens and causing sewage disposal problems. It therefore becomes necessary, although undesirable, to separate the barrier film material from the absorbent article prior to flushing.

In addition to the article itself, typically the packaging in which the disposable article is distributed is also made from a water resistant material. Water resistivity is necessary to prevent the degradation of the packaging from environmental conditions and to protect the disposable articles therein. Although this packaging may be safely stored with other refuse for commercial disposal, and especially in the case of individual packaging of the products, it is often more convenient to dispose of the packaging in the toilet with the discarded disposable article. However, where such packaging is composed of a water resistant material, the aforementioned problems persist.

In an effort to overcome these deficiencies hydrophilic materials can be made, to a degree, hydrophobic. To make a hydrophilic material partially hydrophobic the material has to be treated with a hydrophobic material to impart the desired water resistant properties to the material. The problem with this method is that the material used to impart water repellency to the hydrophilic material may further interfere with the disintegration of the film when flushed, negating any advantage of using a hydrophilic material.

Alternatively, a hydrophobic material can be made, to a degree, hydrophilic. This typically has been achieved by modifying a water resistant material, such as polyethylene, with a hydrophilic monomer such as (meth)acrylic acids, (meth)acrylate esters, hydroxyalkyl (meth)acrylate, polyethylene glycol, and glycidal methacrylate thereby making a hydrophobic material more hydrophilic.

One consideration when modifying the hydrophobic property of the barrier film by blending a hydrophobic polymer with a hydrophilic polymer, is the compatibility of the two polymers. If the two polymers are completely non-compatible then the blended polymers may form films or other articles having poor mechanical and aesthetic compatibilities. Generally, blends of polyolefin with poly (ethylene oxide) are very poor.

SUMMARY OF THE INVENTION

Briefly, the present invention relates to a water-responsive article made from a composition of matter comprising a blend of a hydrophobic polymer and a hydrophilic polymer. In one embodiment, the blend has from about 1 weight percent to about 35 weight percent of a polyolefin, such as a polyethylene or a polypropylene and from about 99 weight percent to about 65 weight percent of poly(ethylene oxide). Generally, the article, such as a film, is water-dispersible.

In another embodiment, a water-responsive article can be made from a composition of matter comprising a blend having from about 1 weight percent to about 55 weight percent of a modified polyolefin and from about 99 weight percent to about 45 weight percent a of poly(ethylene oxide). Desirably, the polyolefin has been modified by having grafted thereto from about 1 weight percent to about 20 weight percent of a compatibilizing monomer.

As used herein, the term "water-responsive" includes article materials that are water-dispersible, water-disintegratable and water-weakened. "Water-dispersible" is used herein to describe a 5 mil (0.005 of an inch) film that, under the water-responsive test described below, dissolves or breaks into pieces smaller than a 20 mesh screen.

"Water-disintegratable" describes a 5 mil film that, under the water-responsive test, breaks into multiple pieces after 2 minutes with some of the pieces caught by a 20 mesh screen. "Water-weakenable" describes a 5 mil film that, under the water-response test, remains in tact but loses rigidity and becomes drapable, i.e., will bend without an external force applied to the film when it is held by one corner at a substantially horizontal position.

Another aspect of the invention provides for a method of making an article from a polyolefin-poly(ethylene oxide) blend composition. The method includes blending under melt conditions specified amounts of either an unmodified or a modified polyolefin with a poly(ethylene oxide). When the polyolefin is unmodified the blend will have from about 1 weight percent to about 35 weight percent of polyolefin and from about 99 weight percent to about 65 weight percent of poly(ethylene oxide). When the polyolefin has been modified by having grafted thereto a compatibilizing monomer the blend will have from about 1 weight percent to about 55 weight percent of the modified polyolefin with from about 99 weight percent to about 45 weight percent of poly (ethylene oxide).

It is an object of the invention to provide a water-responsive composition comprising a polyolefin and a poly (ethylene oxide). More specifically, it is an object of the invention to provide a water-responsive article made from a composition comprising a polyethylene, a polypropylene, a modified polyethylene or a modified polypropylene, and a poly(ethylene oxide).

It is another object of the invention to provide a water-responsive film comprising a polyethylene, a polypropylene, a modified polyethylene or a modified polypropylene, and a poly(ethylene oxide).

It is another object of the invention to provide a water-responsive thermoplastic blend that can be conveniently and economically processed on existing standard manufacturing equipment, in a conventional manner known in the art.

Another object of the invention is to provide a water-responsive thermoplastic blend that will be attractive, economical and capable of being flushed without the adverse effects presently attributed to such products.

DETAILED DESCRIPTION OF THE PREFERRED EMBODIMENTS

Figure 1:
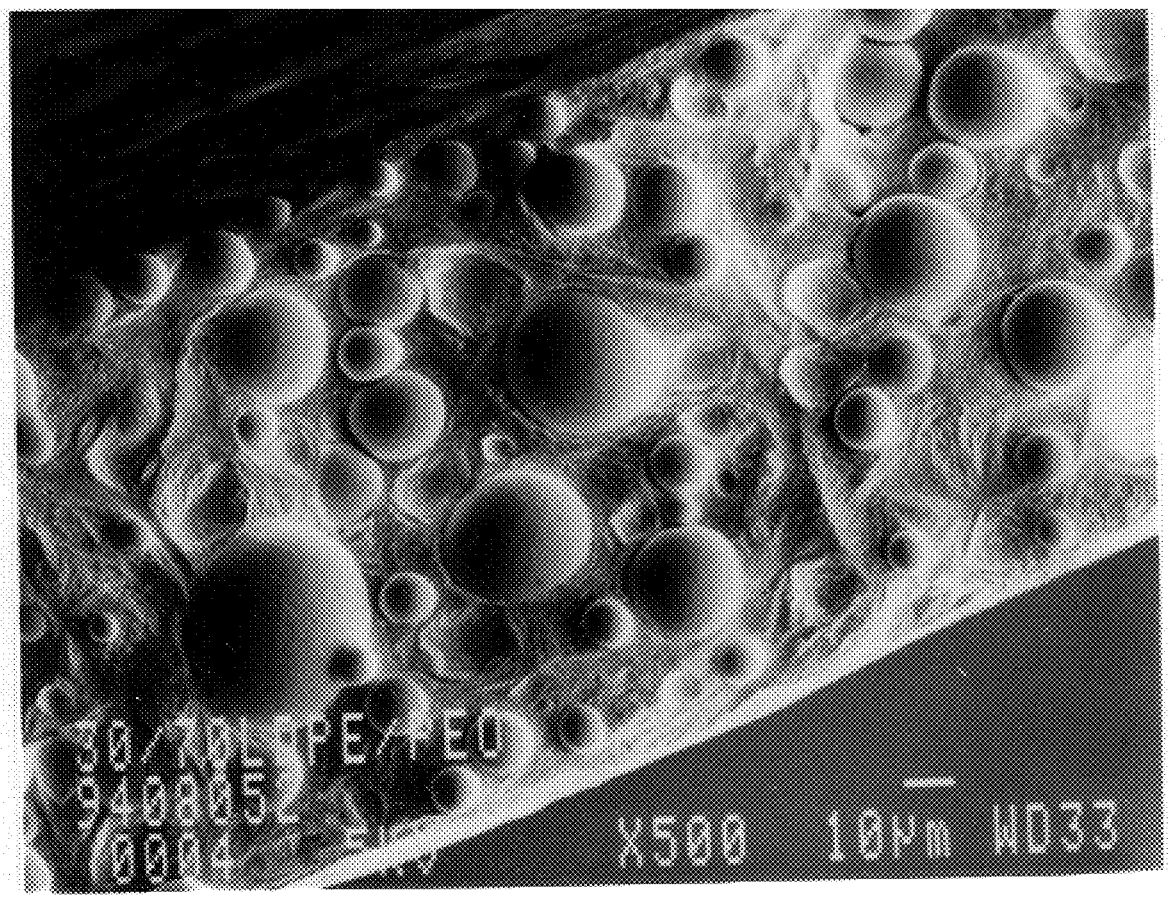
FIG. 1 is a photomicrograph of a film made from a blend of 30 weight percent polyethylene and 70 weight percent poly(ethylene oxide).

The present invention resides in the discovery that a water-responsive, thermoplastic article can be made from a compositional blend of a polyolefin and a poly(ethylene oxide). In accordance with the invention, water-responsiveness for the article can be varied by modifying the polyolefin and by adjusting its ratio in the blend to the amount of poly(ethylene oxide) present in the blend. The saturated ethylene polymers useful in the practice of this invention include homopolymers or copolymers of ethylene and polypropylene and are essentially linear in structure. As used herein, the term "saturated" refers to polymers which are fully saturated, but also includes polymers containing up to about 5% unsaturation. The homopolymers of ethylene include those prepared under either low pressure, i.e., linear low density or high density polyethylene, or high pressure, i.e., branched or low density polyethylene. High density polyethylenes are typically characterized by a density that is about equal to or greater than 0.94 grams per cubic centimeter (g/cc). The high density polyethylenes useful as a base resin in the present invention have a density ranging from about 0.94 g/cc to about 0.97 g/cc. The polyethylenes can have a melt index, as measured at 2.16 kg and 190° C., ranging from about 0.01 decigrams per minute (dg/min) to 100 dg/min. Desirably, the polyethylene has a melt index of 0.01 dg/min to about 50 dg/min and more desirably of 0.05 dg/min to about 25 dg/min. Alternatively, mixtures of polyethylene can be used as the base resin in producing the graft copolymer compositions, and such mixtures can have a melt index greater than 0.005 dg/min to less than about 100 dg/min.

The low density polyethylene has a density of less than 0.94 g/cc and are usually in the range of 0.91 g/cc to about 0.93 g/cc. The low density polyethylene has a melt index ranging from about 0.05 dg/min to about 100 dg/min and desirably from 0.05 dg/min to about 20 dg/min. Ultra low density polyethylene can be used in accordance with the present invention. Generally, ultra low density polyethylene has a density of less than 0.90 g/cc.

Generally, polypropylene has a semi-crystalline structure having a molecular weight of about 40,000 or more, a density of about 0.90 g/cc, a melting point of about 168° C. to about 171° C. for isotactic polypropylene and a tensile strength of 5000 psi. Polypropylene can also have other tacticities including syndiotactic and atactic.

The above polyolefins can also be manufactured by using the well known multiple-site Ziegler-Natta catalysts or the more recent single-site metallocene catalysts. The metallocene catalyzed polyolefins have better-controlled polymer microstructures than polyolefins manufactured using Ziegler-Natta catalysts, including narrower molecular weight distribution, well-controlled chemical composition distribution, comonomer sequence length distribution, and stereoregularity. Metallocene catalysts are known to polymerize propylene into atactic, isotactic, syndiotactic, isotactic-atactic stereoblock copolymer.

Copolymers of ethylene which can be useful in the present invention may include copolymers of ethylene with one or more additional polymerizable, unsaturated monomers. Examples of such copolymers include, but are not limited to, copolymers of ethylene and alpha olefins (such as propylene, butene, hexene or octene) including linear low density polyethylene, copolymers of ethylene and vinyl esters of linear or branched carboxylic acids having 1–24 carbon atoms such as ethylene-vinyl acetate copolymers, and copolymers of ethylene and acrylic or methacrylic esters of linear, branched or cyclic alkanols having 1–28 carbon atoms. Examples of these latter copolymers include ethylene-alkyl (meth)acrylate copolymers, such as ethylene-methyl acrylate copolymers.

Poly(ethylene oxide) resins suitable for the present invention can have a molecular weight ranging from about 100,000 to about 8,000,000. Poly(ethylene oxide) is available from Union Carbide Corporation under the trade name of POLYOX®. Typically, poly(ethylene oxide) is a dry free flowing white powder having a crystalline melting point in the order of about 65° C., above which the poly(ethylene oxide) resin becomes thermoplastic and can be formed by molding, extrusion and other methods known in the art.

In accordance with this invention, a water-dispersible article of manufacture can be produced from a composition of matter comprising blend having about 1 weight percent to about 35 weight percent of an unmodified polyolefin and from about 99 weight percent to about 65 weight percent poly(ethylene oxide). Desirably, the blend has from about 1 weight percent to about 20 weight percent of the polyolefin and from about 99 weight percent to about 80 weight percent poly(ethylene oxide) and more desirably the blend has from about 1 weight percent to about 15 weight percent polyolefin and from about 99 weight percent to about 85 weight percent poly(ethylene oxide).

Surprisingly, water-responsiveness for the article can be varied by modifying the polyolefin and increasing the amount of the modified polyolefin in the blend. Preferably, the polyolefin has been modified by having grafted thereto a compatibilizing monomer. A non-limiting example of a suitable compatibilizing monomer is 2-hydroxyethyl methacrylate. Grafting of the compatibilizing monomer is described in greater detail in the commonly assigned U.S. patent application entitled "METHOD OF MAKING POLYOLEFINS HAVING GREATER THAN 5 PERCENT 2-HYDROXYETHYL METHACRYLATE GRAFTED THERETO" filed Oct. 18, 1996, the disclosure of which is incorporated herein by reference and made a part hereof.

The modified polyolefin constituent of the blend can have as little as 0.1 weight percent of a compatibilizing monomer grafted thereto. Desirably, the modified polyolefin has grafted thereto from about 1 weight percent to about 20 weight percent, based on the weight of polyolefin, of a compatibilizing monomer. Preferably, the modified polyolefin has from about 1 weight percent to about 10 weight percent, based on the weight of polyolefin, of a compatibilizing monomer is grafted to the polyolefin.

In accordance with this invention, a water-responsive article can be produced from a composition of matter comprising a blend having from about 1 weight to about 55 weight percent of a modified polyolefin and from about 99 weight percent to about 45 weight percent poly(ethylene oxide). A water-dispersible article can be produced from a blend having from 1 weight percent to about 35 weight percent of a modified polyolefin and from about 99 weight percent to about 65 weight percent of poly(ethylene oxide). A water disintegratable article can be produced from a blend having from about 35 weight percent to about 45 weight percent of modified polyolefin and from about 65 weight percent to about 55 weight percent of poly(ethylene oxide). A water-weakenable article may be produced from a blend having from about 45 weight percent to about 55 weight percent of a modified polyolefin and form about 55 weight percent to about 45 weight percent of poly(ethylene oxide). Non-limiting examples of water-responsive articles that can be produced from the blends include thermoplastic tampon tubes, garbage bags, thermoplastic films and the like. To have a water response time of less than about 2 minutes, desirably, the wall thickness or caliper of the article, e.g., the tampon applicator or film is 5 mils or less. One would understand that an article having a caliper greater than 5 mils would still be water-responsive but may take longer than 2 minutes after being subjected to water before becoming affected. It is to be understood that, as for a film, "caliper" and "thickness" may be used interchangeably. However, in a shaped article, such as a tube or other configuration having a wall, the caliper of the wall would more accurately describe the thickness measurement.

Processing characteristics of the blends for films can be enhanced by the incorporation of lubricants or slip agents into the blends in an amount up to about 5 weight percent. A typical blend formulation including a lubricant would be in the order of about 75 weight percent of poly(ethylene oxide), about 20 weight percent of a polyolefin and about 5 weight percent of a lubricant. Such lubricants are well known in the art and include Tween 20, Turgitol NP13 available from Union Carbide and various fatty acids such as Kenamide E available from Witco Chemical.

In addition, the blends may contain other components to enhance the properties of the resulting material. For example, polyethylene glycol can be added to lower the melt viscosity of the melted blend to a range suitable for other processes such as meltblown or meltsprayed nonwoven materials. The amount of polyethylene glycol can be from about 0.1 weight percent to about 10 weight percent. Suitable polyethylene glycols are available from Union Carbide under the tradename CARBOWAX®.

Importantly, the water-responsive blends of the present invention are capable of being thermoformed using conventional techniques known in the art but yet do not form a single phase blend morphology. As can be seen from FIGS. 1 and 2, an article formed in accordance with the invention exhibits two-phase morphology where one polymer forms a continuous phase and the second polymer forms a dispersed or discontinuous phase. Articles made from blends of unmodified polyethylene and poly(ethylene oxide) exhibited water-responsiveness at up to about 35 weight percent of unmodified polyethylene. Surprisingly, articles made from blends of modified polyethylene and poly(ethylene oxide) exhibited water-responsiveness up to about 55 weight percent of modified polyethylene.

The polyolefin and poly(ethylene oxide) blends of the invention can be prepared by mixing the desired weight ratio of the constituents into a blend using any standard equipment commonly used for blending thermoplastic resins. For example, a batch or continuous blender may be used to blend the polyolefin and poly(ethylene oxide) using heat and high shear. Although not preferred, a single screw or twin screw extruder which utilize various mixing screw sections, kneading sections and the like can be used. After melt blending, the blend can be solidified and pelletized or extruded into a film using techniques known in the art.

The present invention is illustrated in greater detail by the specific examples presented below. It is to be understood that these are illustrative embodiments and are not intended to be limiting of the invention, but rather are to be construed broadly within the scope and content of the appended claims. In all the examples, a relatively short but determinable disintegration time was desired.

In each of the examples below, 5 mil films were prepared from the melt blends using a Carver hot press with two heated platens at a temperature of 190° C. and a pressure of 15000 psi for 3 minutes.

Water-Response Test:

To determine the water-responsiveness of an article, a blend, in accordance with this invention, was pressed into a film. A section of the film measuring about 0.25 of an inch by about 0.5 of an inch was removed. Using a pair of tweezers to hold the section of film, it was immersed into a scintillation vial filled with 20 milliliters of water and held for 2 minutes. After 2 minutes, if the film begin to disperse or disintegrate, the contents of the scintillation vial were emptied through a "20 mesh" U.S.A. Standard Testing Sieve (ASTME-11 Specification, No. 20).

If the film did not disperse or disintegrate, the film was held immersed in the water for additional 3 minutes to observe any loss in rigidity. The vial was rinsed with 20 milliliter of water from a squeeze bottle and emptied through the sieve.

In the examples the following terms are used to describe the effect of water on the section of film:

Water-dispersible: the film dissolves or breaks into pieces smaller than a 20 mesh screen after 2 minutes.

Water-disintegratable: the film breaks into multiple pieces after 2 minutes with some of film caught by a 20 mesh screen.

Water-weakenable: the film remains in one piece but weakens and loses rigidity significantly in 5 minutes.

Water-stable: the film remains in one piece and does not lose any of its rigidity after 5 minutes.

EXAMPLE 1

A blend containing 21 grams of low density polyethylene having a melt index of 1.9 g/10 minute (available from Dow Chemical) and 21 grams of poly(ethylene oxide), poly (ethylene oxide), having a molecular weight of 200,000 g/mol (POLYOX® WSR N-80 is available from Union Carbide) was prepared using a Haake Rheomix 600 twin-roller mixer, (available from Haake, 53 West Century Rd. Paramus, N.J., 07652). Each zone of the Haake mixer was preheated to 180° C. The material was mixed for 20 minutes at a screw speed of 150 rpm. After 20 minutes, the melt was removed from the mixer and cooled in air.

The film was determined to be water-stable.

EXAMPLE 2

The constituents of Example 1 were blended using 12.6 grams of low density polyethylene and 29.4 grams of poly(ethylene oxide) in the Haake Rheomix mixer for 20 minutes at a screw speed of 150 rpm. After 20 minutes, the melt was removed from the mixer and cooled in air. FIG. 1 is a photomicrograph of the fracture surface of a 5 mil film of this composition using scanning electron microscopy.

The film was determined to be water-dispersible.

EXAMPLE 3

The constituents of Example 1 were blended using 4.2 grams of low density polyethylene and 37.8 grams of poly(ethylene oxide) in a HAAKE Rheomix mixer for 20 minutes at a screw speed of 150 rpm. After 20 minutes, the melt was removed from the mixer and cooled in air.

The film was determined to be water-dispersible.

EXAMPLE 4

A blend containing 21 grams of a modified low density polyethylene and 21 grams of poly(ethylene oxide) was prepared using the Haake Rheomix mixer for 20 minutes at a screw speed of 150 rpm. After 20 minutes, the melt was removed from the mixer and cooled in air. The low density polyethylene was modified by grafting 11.1 weight percent of a compatibilizing monomer, (2-hydroxyethyl methacrylate) to the polyethylene.

The film was determined to be water-weakenable.

EXAMPLE 5

A blend containing 18.9 grams of a modified low density polyethylene of Example 4 and 23.1 grams of poly(ethylene oxide) was prepared using the Haake Rheomix mixer for 20 minutes at a screw speed of 150 rpm. After 20 minutes, the melt was removed from the mixer and cooled in air.

The film was determined to be water-disintegratable. The film lost rigidity and curled after 19 seconds and began forming fibers after 69 seconds. The film began to disintegrate after 90 seconds.

EXAMPLE 6

A blend containing 16.8 grams of a modified low density polyethylene of Example 4 and 25.2 grams of poly(ethylene oxide) was prepared using the Haake Rheomix mixer for 20 minutes at a screw speed of 150 rpm. After 20 minutes, the melt was removed from the mixer and cooled in air.

The film was determined to be water-disintegratable. The film lost rigidity and curled after 11 seconds and began forming fibers after 61 seconds. The film began to disintegrate after 90 seconds.

EXAMPLE 7

A blend containing 14.7 grams of a modified low density polyethylene of Example 4 and 27.3 grams of poly(ethylene oxide) was prepared using the Haake Rheomix mixer for 20 minutes at a screw speed of 150 rpm. After 20 minutes, the melt was removed from the mixer and cooled in air.

The film was determined to be water-disintegratable. The film lost rigidity and curled after 10 seconds and began forming fibers after 33 seconds. The film began to disintegrate after 33 seconds.

EXAMPLE 8

Figure 2:
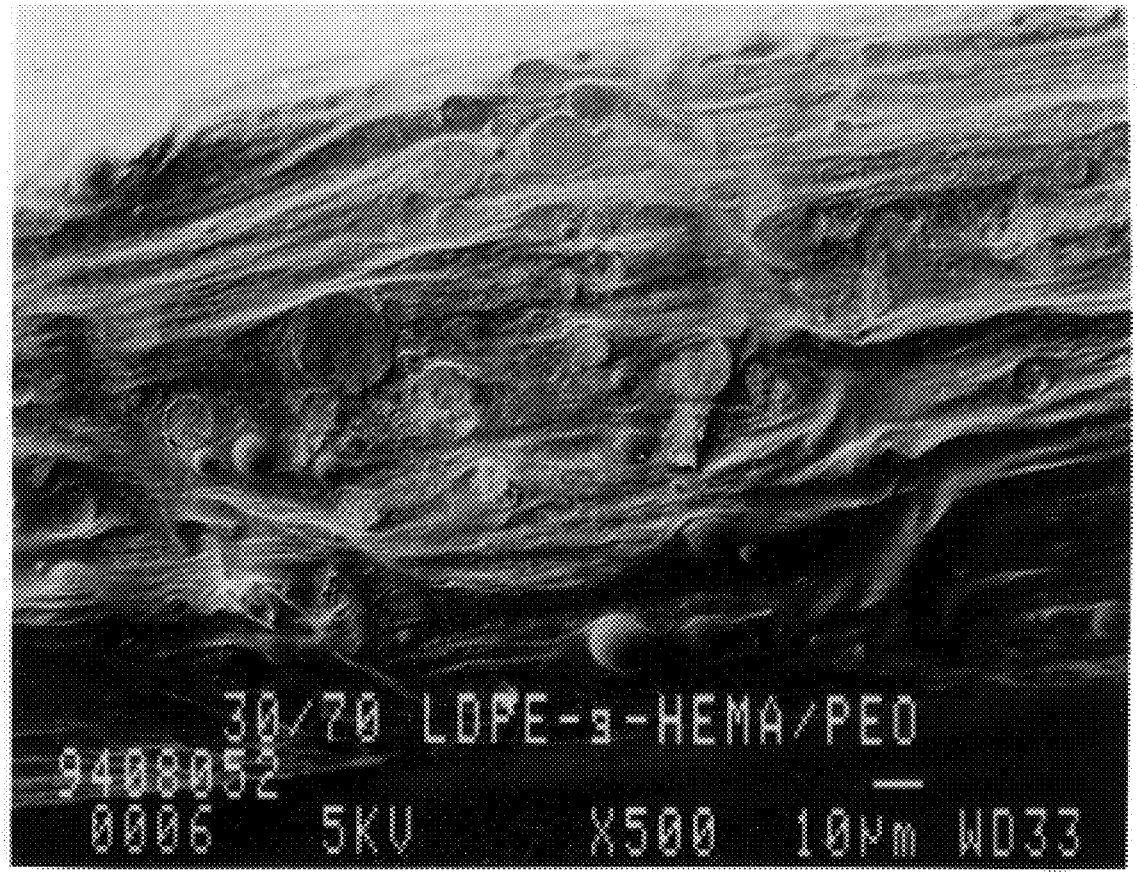
FIG. 2 is a photomicrograph of a film made from a blend of 30 weight percent of a modified polyethylene and 70 weight percent poly(ethylene oxide).

A blend containing 12.6 grams of a modified low density polyethylene of Example 4 and 29.4 grams of poly(ethylene oxide) was prepared using the Haake Rheomix mixer for 20 minutes at a screw speed of 150 rpm. After 20 minutes, the melt was removed from the mixer and cooled in air. FIG. 2 is a photomicrograph of the fracture surface of a 5 mil film of this composition using scanning electron microscopy.

The film was determined to be water-dispersible.

EXAMPLE 9

A blend containing 4.2 grams of a modified low density polyethylene of Example 4 and 37.8 grams of poly(ethylene oxide) was prepared using the Haake Rheomix mixer for 20 minutes at a screw speed of 150 rpm. After 20 minutes, the melt was removed from the mixer and cooled in air.

The film was determined to be water-dispersible.

While the invention has been described with reference to preferred embodiments of the invention, it is to be appreciated that various substitutions, changes, omissions and modifications may be made without departing from the scope of the invention as defined by the appended claims.

We claim:

1. A composition of matter comprising a blend of from about 1 weight percent to about 35 weight percent of a 2-hydroxyethyl methacrylate grafted polyolefin and from about 99 weight percent to about 65 weight percent of poly(ethylene oxide).

2. The composition of matter of claim 1 wherein said blend comprises from about 1 weight percent to about 20 weight percent of a 2-hydroxyethyl methacrylate grafted polyolefin and from about 99 weight percent to about 80 weight percent of poly(ethylene oxide).

3. The composition of matter of claim 1 wherein said blend comprises from about I weight percent to about 15 weight percent of a 2-hydroxyethyl methacrylate grafted polyolefin and from about 99 weight percent to about 85 weight percent of poly(ethylene oxide).

4. The composition of matter of claim 1 wherein said polyolefin is polyethylene.

5. The composition of matter of claim 1 wherein said polyolefin is polypropylene.

6. A water-dispersible article comprising from about 1 weight percent to about 35 weight percent of a 2-hydroxyethyl methacrylate grafted polyolefin and from about 99 weight percent to about 65 weight percent of poly(ethylene oxide).

7. The water-dispersible article of claim 6 wherein said 2-hydroxyethyl methacrylate grafted polyolefin has grafted thereto from about 1 weight percent to about 20 weight percent of 2-hydroxyethyl methacrylate monomer.

8. The water-dispersible article of claim 6 having a caliper of 5 mils or less.

9. A method of making a water-responsive article comprising the steps of blending under melt conditions from about 1 weight percent to about 55 weight percent of a modified polyolefin and from about 99 weight percent to about 45 weight percent poly(ethylene oxide) and forming a water-responsive article from said blend, wherein said modified polyolefin is a polyolefin having grafted thereto from about 1 weight percent to about 20 weight percent of 2-hydroxyethyl methacrylate, based on the weight of the polyolefin.

10. A composition of matter comprising a blend of from about 1 weight percent to about 55 weight percent of a modified polyolefin and from about 99 weight percent to about 45 weight percent of poly(ethylene oxide), wherein said modified polyolefin is a 2-hydroxyethyl methacrylate grafted polyolefin.

11. The composition of matter of claim 10 wherein said modified polyolefin is a polyolefin having grafted thereto from about 1 weight percent to about 20 weight percent, based on the weight of polyolefin, of 2-hydroxyethyl methacrylate monomer.

12. The composition of matter of claim 10 wherein said modified polyolefin is a polyolefin having grafted thereto from about 1 weight percent to about 10 weight percent, based on the weight of polyolefin, of 2-hydroxyethyl methacrylate monomer.

13. The composition of matter of claim 10 comprising a blend of from about 1 weight percent to about 35 weight percent of a modified polyolefin selected from the group consisting of polyethylene and polypropylene and from about 99 weight percent to about 65 weight percent of poly(ethylene oxide) wherein a film made from said blend is water-dispersible.

14. The composition of matter of claim 10 comprising a blend of from about 35 weight percent to about 45 weight percent of a modified polyolefin selected from the group consisting of polyethylene and polypropylene and from about 65 weight percent to about 55 weight percent of poly(ethylene oxide) wherein a film made from said blend is water-disintegratable.

15. The composition of matter of claim 10 comprising a blend of from about 45 weight percent to about 55 weight percent of a modified polyolefin selected from the group consisting of polyethylene and polypropylene and from about 55 weight percent to about 45 weight percent of poly(ethylene oxide) wherein a film made from said blend is water-weakenable.

16. The composition of matter of claim 10 wherein said modified polyolefin has a melt index of from about 0.01 decigrams per minute to about 100 decigrams per minute at 2.16 kg and 190° C.

17. A method of making a water-disintegratable article comprising the steps of blending under melt conditions from about 35 weight percent to about 45 weight percent of a modified polyethylene and from about 65 weight percent to about 55 weight percent of poly(ethylene oxide); and forming a water-disintegratable article from said blend; wherein said modified polyethylene is a polyethylene having grafted thereto from about 1 weight percent to about 20 weight percent of 2-hydroxyethyl methacrylate, based on the weight of the polyethylene.

18. A method of making a water-weakenable article comprising the steps of blending under melt conditions from about 45 weight percent to about 55 weight percent of a modified polyethylene and from about 55 weight percent to about 45 weight percent of poly(ethylene oxide); and forming a water-weakened article from said blend wherein said modified polyethylene is a polyethylene having grafted thereto from about 1 weight percent to about 10 weight percent of 2-hydroxyethyl methacrylate, based on the weight of the polyethylene.

19. A water-responsive article comprising from about 1 weight percent to about 55 weight percent of a modified polyolefin and from about 99 weight percent to about 45 weight percent of poly(ethylene oxide), wherein said modified polyolefin is a polyolefin having grafted thereto from about 1 weight percent to about 20 weight percent of 2-hydroxyethyl methacrylate, based on the weight of polyolefin.

20. The water-responsive article of claim 19 wherein said modified polyolefin is polyethylene or polypropylene.

21. The water-responsive article of claim 19 wherein said modified polyolefin is a polyolefin having grafted thereto from about 1 weight percent to about 10 weight percent of 2-hydroxyethyl methacrylate, based on the weight of the polyolefin.

22. The water-responsive article of claim 19 comprising from about 1 weight percent to about 35 weight percent of said modified polyolefin and from about 99 weight percent to about 65 weight percent of poly(ethylene oxide) wherein said article is water-dispersible.

23. The water-responsive article of claim 19 comprising from about 35 weight percent to about 45 weight percent of said modified polyolefin and from about 65 weight percent to about 55 weight percent of poly(ethylene oxide) wherein said article is water-disintegratable.

24. The water-responsive article of claim 19 comprising from about 45 weight percent to about 55 weight percent of said modified polyolefin and from about 55 weight percent to about 45 weight percent of poly(ethylene oxide) wherein said article is water-weakenable.

25. A method of making a water-dispersible article comprising the steps of blending under melt conditions from about 1 weight percent to about 35 weight percent of a 2-hydroxyethyl methacrylate grafted polyolefin and from about 99 weight percent to about 65 weight percent of a poly(ethylene oxide) and forming a water-dispersible article from said blend.

26. The method of claim 25 wherein said 2-hydroxyethyl methacrylate grafted polyolefin has grafted thereto from about 1 weight percent to about 20 weight percent, based on the weight of the polyolefin, of 2-hydroxyethyl methacrylate.

\* \* \* \* \*